United States Patent
Vad et al.

(10) Patent No.: US 8,608,665 B2
(45) Date of Patent: Dec. 17, 2013

(54) METHODS FOR PRESSURE DETECTION

(76) Inventors: Vijay Vad, New York, NY (US);
Christian Haller, Alexandria, VA (US);
David Mandel, Washington, DC (US)

(*) Notice: Subject to any disclaimer, the term of this patent is extended or adjusted under 35 U.S.C. 154(b) by 21 days.

(21) Appl. No.: 13/211,121

(22) Filed: Aug. 16, 2011

(65) Prior Publication Data

US 2011/0298628 A1 Dec. 8, 2011

Related U.S. Application Data

(62) Division of application No. 12/323,154, filed on Nov. 25, 2008, now abandoned.

(60) Provisional application No. 61/097,854, filed on Sep. 17, 2008.

(51) Int. Cl.
*A61B 5/03* (2006.01)

(52) U.S. Cl.
USPC ......... 600/561; 600/587; 340/573.1; 604/118

(58) Field of Classification Search
USPC ................ 340/573.1; 600/561, 587; 604/118
See application file for complete search history.

(56) References Cited

U.S. PATENT DOCUMENTS

| | | | |
|---|---|---|---|
| 3,730,168 A | | 5/1973 | McWhorter |
| 4,175,567 A | * | 11/1979 | Patel .............................. 600/561 |
| 4,192,319 A | | 3/1980 | Hargens et al. |
| 4,215,699 A | * | 8/1980 | Patel .............................. 600/561 |
| 4,576,181 A | | 3/1986 | Wallace et al. |
| 4,723,938 A | * | 2/1988 | Goodin et al. ............. 604/97.02 |
| 4,759,750 A | | 7/1988 | DeVries et al. |
| 4,804,054 A | | 2/1989 | Howson et al. |
| 4,919,653 A | * | 4/1990 | Martinez et al. ............... 604/117 |
| 5,085,631 A | * | 2/1992 | Leighton ......................... 604/28 |
| 5,106,376 A | * | 4/1992 | Mononen et al. ......... 604/164.11 |
| 5,163,904 A | | 11/1992 | Lampropoulos et al. |
| 5,209,721 A | * | 5/1993 | Wilk ................................ 604/26 |
| 5,279,308 A | * | 1/1994 | DiSabito et al. .............. 600/588 |
| 5,353,800 A | | 10/1994 | Pohndorf et al. |

(Continued)

FOREIGN PATENT DOCUMENTS

| | | |
|---|---|---|
| EP | 0538259 A1 | 2/1991 |
| WO | WO 92/15256 A1 | 9/1992 |

OTHER PUBLICATIONS

Bliddal, Placement of Intra-Articular Injections Verified by Mini Air-Arthrography, *Ann Rheum Dis.* (Oct. 1999), 58(10):641-643.

(Continued)

*Primary Examiner* — Sean Dougherty

(57) ABSTRACT

A device may include a first locking mechanism configured to connect a first end of the device to a needle, a second locking mechanism configured to connect a second end of the device to a syringe, a pressure transducer, a microprocessor and a light emitting diode. The pressure transducer may be configured to measure a first pressure at a first time and a second pressure at a second time. The microprocessor may be configured to receive the first pressure and the second pressure from the pressure transducer, determine a pressure difference between the first pressure and the second pressure, and determine a time difference between the first time and the second time. The light emitting diode may be configured to signal when the needle is properly situated based on the pressure difference and the time difference.

21 Claims, 5 Drawing Sheets

210

(56) References Cited

U.S. PATENT DOCUMENTS

| | | | |
|---|---|---|---|
| 5,421,821 A | 6/1995 | Janicki et al. | |
| 5,453,091 A * | 9/1995 | Taylor et al. | 604/100.03 |
| 5,526,820 A | 6/1996 | Khoury | |
| 5,694,946 A * | 12/1997 | Tenerz et al. | 600/561 |
| 5,902,273 A | 5/1999 | Yang et al. | |
| 6,086,559 A * | 7/2000 | Enk | 604/121 |
| 6,117,086 A | 9/2000 | Shulze | |
| 6,190,370 B1 | 2/2001 | Tsui | |
| 6,866,648 B2 | 3/2005 | Hadzic et al. | |
| 7,175,608 B2 | 2/2007 | Hasan et al. | |
| 7,364,567 B2 | 4/2008 | Beyerlein | |
| 7,727,224 B2 | 6/2010 | Hadzic et al. | |
| 7,775,985 B2 | 8/2010 | Eide | |
| 8,282,565 B2 * | 10/2012 | Mahapatra et al. | 600/486 |
| 2002/0016567 A1 * | 2/2002 | Hochman et al. | 604/131 |
| 2002/0052574 A1 | 5/2002 | Hochman et al. | |
| 2004/0186430 A1 * | 9/2004 | Hasan et al. | 604/118 |
| 2005/0004518 A1 | 1/2005 | Call | |
| 2005/0043710 A1 | 2/2005 | Hadzic et al. | |
| 2006/0122555 A1 * | 6/2006 | Hochman | 604/67 |
| 2006/0149161 A1 * | 7/2006 | Wilson et al. | 600/561 |
| 2006/0173480 A1 | 8/2006 | Zhang | |
| 2006/0247657 A1 | 11/2006 | Trieu | |
| 2007/0060822 A1 * | 3/2007 | Alpert et al. | 600/481 |
| 2007/0060835 A1 * | 3/2007 | Eide | 600/561 |
| 2007/0123781 A1 * | 5/2007 | Callahan et al. | 600/483 |
| 2007/0235083 A1 | 10/2007 | Dlugos | |
| 2008/0009978 A1 * | 1/2008 | Smirnov | 700/282 |
| 2008/0015406 A1 | 1/2008 | Dlugos et al. | |
| 2008/0039897 A1 * | 2/2008 | Kluge et al. | 607/17 |
| 2008/0132926 A1 | 6/2008 | Eichmann et al. | |
| 2008/0154188 A1 * | 6/2008 | Hochman | 604/67 |
| 2008/0281278 A1 * | 11/2008 | Williams et al. | 604/264 |
| 2010/0094143 A1 * | 4/2010 | Mahapatra et al. | 600/486 |
| 2010/0094229 A1 | 4/2010 | Scarborough et al. | |
| 2011/0125107 A1 * | 5/2011 | Slocum et al. | 604/272 |
| 2011/0202012 A1 * | 8/2011 | Bartlett | 604/218 |

OTHER PUBLICATIONS

Cleary et al., Intra-Articular Corticosteroid Injections in Juvenile Idiopathic Arthritis, *Arch Dis Child.* (Mar. 2003), 88(3):192-196.

Esenyel et al., Comparison of Four Different Intra-Articular Injection Sites in the Knee: A Cadaver Study, *Knee Surg Sports Traumatol Arthrosc.* (May 2007), 15(5):573-577.

Glattes et al., A Simple, Accurate Method to Confirm Placement of Intra-Articular Knee Injection, *Am J Sports Med.* (Jun. 2004), 32(4):1029-1031.

Jackson et al., Accuracy of Needle Placement Into the Intra-Articular Space of the Knee, *J Bone Joint Surg Am.* (Sep. 2002), 84-A(9):1522-1527.

Jones et al., Importance of Placement of Intra-Articular Steroid Injections, *BMJ* (Nov. 20, 1993), 307(6915):1329-1330.

Lockman, Practice Tips: Knee Joint Injections and Aspirations: The Triangle Technique, *Can Fam Physician* (Nov. 2006), 52(11):1403-1404.

Letters to the Editor, *J Bone Joint Surg Am.* (Dec. 2003), 85-A(12):2481-2488.

* cited by examiner

METHODS FOR PRESSURE DETECTION

CLAIM OF PRIORITY AND RELATED APPLICATION

This application claims priority to, and is a divisional of, U.S. patent application Ser. No. 12/323,154, entitled "Method and Apparatus for Pressure Detection," filed on Nov. 25, 2008, and U.S. Provisional Patent Application No. 61/097,854, entitled "Pressure Detection Device," filed on Sep. 17, 2008, each of which is hereby incorporated by reference in its entirety.
Not Applicable

BACKGROUND

Osteoarthritis is a degenerative joint disease characterized by abnormal wearing of cartilage that covers and cushions the joint and the destruction or decrease in synovial fluid that lubricates the joint. Treatment for this condition includes injections of medication into the joint which supplements the viscosity of the joint fluid, lubricates and cushions the joint, and produces an analgesic effect. Medication, such as hyaluronic acid, can also have a positive biochemical effect on cartilage cells by slowing or even reversing their deterioration. The key to such treatment is to ensure that the injection is provided precisely into the synovial joint. If the injection is not provided precisely into the synovial joint, the efficacy of the treatment suffers severely. The current technique for locating the needle in this joint is by "feel" of a practiced physician. Studies by Jackson et al. (JBJS 2002) have shown that 30% of the hyaluronic acid injections in knees are improperly placed.

Epidural injections and anesthesia are often given to patients without proper guidance. In particular, proper guidance is necessary for intra-operative anesthesia and for labor and delivery. Improper placement of these procedures can cause dural punctures in up to 1% of individuals. Dural punctures can lead to severe headaches and a need for a blood patch. In rare instances, accidental intravascular injectate may result in paralysis.

SUMMARY

In an embodiment, a pressure detection device may include a small, sterile, inexpensive, disposable, battery-powered attachment to a standard syringe. In an embodiment, the pressure detection device may be embedded inside of a syringe. At the time of use, the device may be assembled by a medical professional and placed between a syringe and an injection needle hub. During the injection process, the device may monitor the pressure at the tip of the needle as the needle is inserted into a patient. As the tip of the needle is positioned in the correct location for injection, the device may detect the pressure change and may alert a physician. The physician may then inject the medication, remove the needle from the patient, and dispose of the entire assembly.

In an embodiment, the device may include a pressure transducer, a power source, a control microprocessor, an interface to the user such as a light emitting diode (LED) and any necessary intermediate circuitry such as, but not limited to, an amplifier, a filter and/or signal processing circuitry. Any or all of these components may be included within a small plastic housing that allows the device to interface with both a standard syringe and a standard needle hub.

In an embodiment, a device may include a first locking mechanism configured to connect a first end of the device to a needle and a second locking mechanism configured to connect a second end of the device to a syringe. The device may include a pressure transducer configured to measure a first pressure at a first time and a second pressure at a second time. The device may include a microprocessor configured to receive the first pressure and the second pressure from the pressure transducer, determine a pressure difference between the first pressure and the second pressure, and determine a time difference between the first time and the second time. The device may include a light emitting diode configured to signal when the needle is properly situated based on the pressure difference and the time difference.

In an embodiment, the device may include a microsensor configured to produce an electrical signal. The device may include a power source configured to power the pressure transducer and the microprocessor. The device may include an external housing made from a biocompatible plastic. The device may include a user interface configured to display the first pressure and the second pressure. In an embodiment, the device may include the pressure transducer further configured to output a voltage signal, an amplifier configured to amplify the output voltage signal, a filter configured to reduce system noise from the pressure transducer, and signal processing circuitry configured to ensure that the output voltage signal is compatible with the microprocessor. The device may be disposable.

In an alternate embodiment, a syringe may include a pressure detection device embedded in the syringe. The pressure detection device may include a pressure transducer configured to measure a first pressure at a first time and a second pressure at a second time. The pressure detection device may include a microprocessor. The microprocessor may be configured to receive the first pressure and the second pressure from the pressure transducer, determine a pressure difference between the first pressure and the second pressure, and determine a time difference between the first time and the second time. The pressure detection device may include a light emitting diode configured to signal when the needle is properly situated based on the pressure difference and the time difference. In an embodiment, the syringe may include a power source configured to power the pressure transducer and the microprocessor in the pressure detection device.

In an embodiment, a method of using a pressure detection device may include obtaining a first pressure at a first time and a second pressure at a second time in real time via a pressure transducer. A pressure difference between the first pressure and the second pressure may be determined. A time difference between the first time and the second time may be determined. A first determination may be performed to determine whether the pressure difference divided by the time difference is less than a slope threshold. The pressure detection device may signal whether the needle is properly situated based on the first determination.

In an embodiment, the pressure detection device may be positioned between a syringe and an injection needle hub. In an embodiment, the first pressure may be an atmospheric pressure and the second pressure may be a cavity pressure. In an embodiment, signaling whether the needle is properly situated may include displaying a light from a light emitting diode and/or producing an audible sound. In an embodiment, the first pressure may be stored. The first pressure may be retrieved to display on a user interface.

In an embodiment, a pressure threshold determination may be performed to determine whether the pressure difference exceeds a pressure threshold. A time threshold determination may be performed to determine whether the time difference is less than a time threshold. Signaling whether the needle is properly situated may be, further based on the pressure threshold determination and the time threshold determination.

In an embodiment, it may be determined whether the second pressure is less than a pressure value. Signaling whether the needle is properly situated may be further based on whether the second pressure is less than the pressure value. In an embodiment, an internal air volume inside the pressure detection device may be determined. The internal air volume may be less than 0.5 mL. In an embodiment, the slope threshold may be approximately −1.5.

In an embodiment, a third pressure may be obtained at a third time. A second determination may be performed to determine whether the third pressure is less than a pressure threshold. A third determination may be performed to determine whether a second time difference between the second time and the third time is greater than a time threshold. Signaling whether the needle is properly situated may be further based on the second determination and the third determination. In an embodiment, the time threshold may be approximately 0.1 seconds. In an embodiment, the pressure threshold may be approximately −0.2 mmHg.

In an embodiment, a system may include a device and a computing system. The device may include a first locking mechanism configured to connect a first end of the device to a needle, a second locking mechanism configured to connect a second end of the device to a syringe, and a pressure transducer configured to measure a first pressure at a first time and a second pressure at a second time. The computing system may be configured to receive the first pressure and the second pressure from the pressure transducer, determine a pressure difference, and perform a second determination to determine a time difference.

BRIEF DESCRIPTION OF THE DRAWINGS

Aspects, features, benefits and advantages of the embodiments described herein will be apparent with regard to the following description, appended claims, and accompanying drawings where:

DETAILED DESCRIPTION

Before the present methods are described, it is to be understood that this invention is not limited to the particular systems, methodologies or protocols described, as these may vary. It is also to be understood that the terminology used herein is for the purpose of describing particular embodiments only, and is not intended to limit the scope of the present disclosure which will be limited only by the appended claims.

As used herein and in the appended claims, the singular forms "a," "an," and "the" include the plural reference unless the context clearly dictates otherwise. Thus, for example, reference to a "needle" is a reference to one or more needles and equivalents thereof known to those skilled in the art, and so forth. Unless defined otherwise, all technical and scientific terms used herein have the same meanings as commonly understood by one of ordinary skill in the art. As used herein, the term "comprising" means "including, but not limited to."

Figure 1:
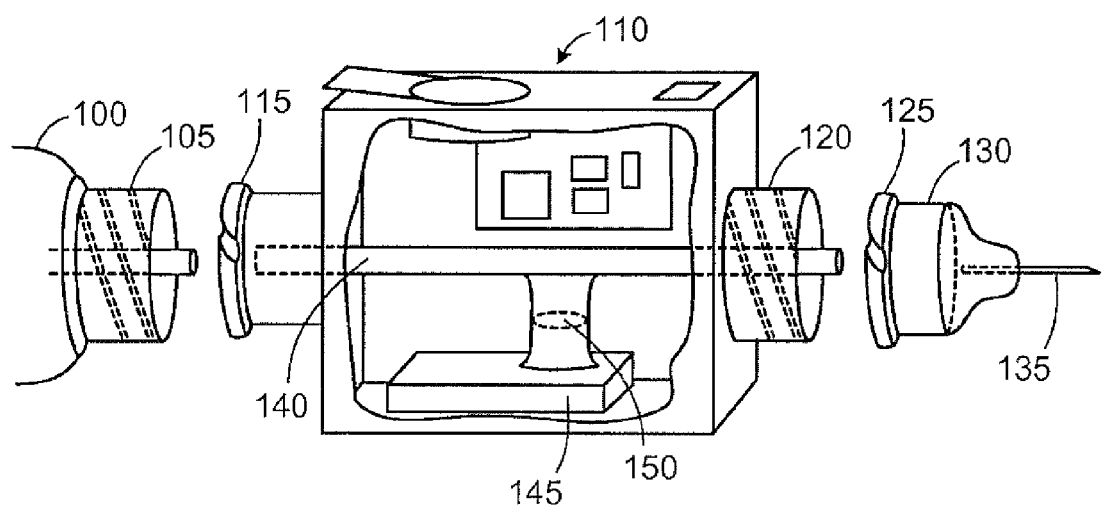
FIG. 1 discloses an exemplary pressure detection device adapted to be placed between a syringe and a needle hub according to an embodiment.

FIG. 1 discloses an exemplary pressure detection device configured to be placed between a syringe and a needle hub according to an embodiment. In an embodiment, a pressure detection device 110 may use pressure sensing technology and recognition algorithms to accurately detect when a needle 135 is properly situated in a patient prior to injection. In an embodiment, the device 110 may be an osteoarthritis pressure detection device. The device 110 may be used for injections into the joint cavity or the epidural space. The device may be used for injections in mammals such as, but not limited to, humans, horses, dogs and sheep. In an embodiment, the device may be used for injections in for example, the knee, shoulder, hip, ankle, elbow or spine.

In an embodiment, the device 110 may be used to inject medication, such as, but not limited to, hyaluronic acid, hyaluronic acid-based hydrogel and/or other biological treatments, into the synovial joint. In an embodiment, the injection of the medication may be used for the treatment of osteoarthritis. In an embodiment, the device 110 may be used to inject medication, such as, but not limited to, anesthetic, anti-inflammatory medications and/or other such treatments, to the epidural space.

After injecting a patient with a medication, the needle 135 may be removed from the patient and the device 110, along with the needle, may be disposed. Because the device 110 ensures that the injection occurs in the proper location, complications such as, but not limited to, a misplaced needle, a reinsertion, an infection from reinsertion, repeated injections and/or additional tissue trauma may be eliminated.

In an embodiment, the device 110 may be sterile, inexpensive and battery-powered. The device 110 may be attached to a standard syringe or may be embedded in a syringe. In an embodiment, the device may be embedded inside a syringe for epidural application.

In an embodiment, the device 110 may be no larger than approximately 1 inch by approximately 1.5 inch by approximately 3 inches. In an embodiment, the device 110 may be no larger than approximately 1 inch by approximately 1 inch by approximately 2 inches. In an embodiment, the device 110 may be approximately 0.5 inches by approximately 0.5 inches by approximately 1.2 inches. In an embodiment, the device 110 may not be longer than approximately 1.5 inches, not including the one or more locking mechanisms. In an embodiment, the device 110 may be approximately 1 inch by approximately 1 inch in a cross-section perpendicular to the length-wise axis. In an embodiment, the device 110 may not weigh more than approximately 25 grams.

In an embodiment, the device 110 may be self-contained or independent. The device 110 may not need to interface electrically with any other devices as it may be a stand alone self-powered device. For example, the device 110 may be battery-powered. In an embodiment, the device 110 may be disposable. The device 110 may be a one-time use device. In an embodiment, the device 110 may be embedded in the syringe for epidural application and after use of the device 110, the syringe, with the embedded device, may be disposed.

In an embodiment, the device 110 may be placed between the barrel of the syringe 100 and an injection needle hub 130. In an embodiment, the device 110 may have a hermetically sealed connection to both the syringe 100 and the needle hub 130. In an embodiment, the device 110 may interface mechanically with any standard syringe 100 and/or needle hub 130 via a standard locking mechanism on each end of the device. For example, the locking mechanism may be, but is not limited to, a luer lock. For example, a female luer lock 105 of the syringe 100 may connect to the device 110 via a male luer lock 115. Similarly, the other end of the device 110 may have a female luer lock 120 to connect to a male luer lock 125 of the needle hub 130. The device 110 may adapt to any over-the-counter generic needle hub 130, syringe 100 and/or catheter system.

During the injection process, the device 110 may monitor the pressure as the needle is inserted into the patient. In an embodiment, the medication may flow from the syringe 100 to the device 110 via the fluid path 140 to the needle 135. In an embodiment, the device 110 may be at least partially transparent to allow a user to determine if there is fluid located in the fluid path.

Figure 2:
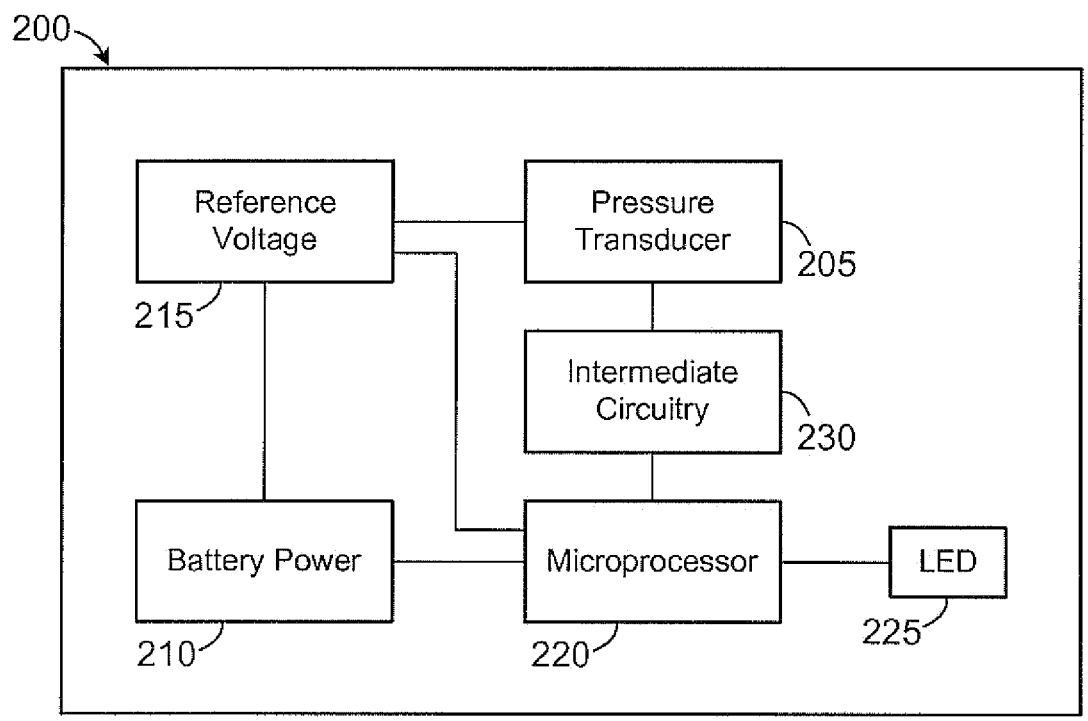
FIG. 2 discloses a block diagram of an exemplary pressure detection device according to an embodiment.

FIG. 2 discloses exemplary components of a pressure detection device according to an embodiment. In an embodiment, the device may include an external housing 200. The material of the external housing 200 may be made of a biocompatible plastic. In an embodiment, the external housing 200 may include a material such that any patient contact with the material will be completely safe for the patient. Additionally, the external housing 200 may be constructed in a manner that minimizes the risk of tearing the physician's gloves.

Inside the external housing 200, the device may include a pressure transducer 205, a power source 210, a control microprocessor 220, an interface to the user such as a light emitting diode (LED) 225 and any necessary intermediate circuitry 230 such as, but not limited to, an amplifier, a filter and/or signal processing circuitry.

In an embodiment, the device may include a pressure transducer 205. As the tip of the needle is positioned in the proper location for injection in the joint cavity or epidural space, the pressure transducer 205 may detect a pressure change. Referring back to FIG. 1, the pressure transducer 145 may determine the pressure through a biocompatible membrane 150. A pressure difference may be determined because there is a pressure differential between a cavity and the atmosphere. In an embodiment, the pressure transducer 145 may sense when the needle 135 has reached the correct injection site via detection of a small pressure change with respect to surrounding atmospheric pressure. In an embodiment, for a knee joint during needle insertion the pressure may decrease by approximately 0.5 mmHg to approximately 4 mmHg. If the injection site is in a joint cavity, the pressure transducer 145 may be able to determine the proper injection site because pressure differences exist between the synovial space and surrounding tissue. In an embodiment, for the epidural space, the pressure may decrease by approximately 0.5 mmHg to approximately 15 mmHg during needle insertion.

In an embodiment, the pressure transducer may include a piezoresistive material formed into a die. The pressure transducer may be a piezoresistive silicon die. When pressure is applied to the die, the electrical resistance of the silicon may change linearly. By applying a constant voltage to the die, the differential output voltage may be measured to determine the applied pressure. The pressure transducer input may be a pressure, and its output may be a voltage proportional to the applied pressure.

In an embodiment, the pressure transducer may include an internal analog to digital converter (ADC). The ADC may internally amplify the millivolt signal from the piezoresistive die and may convert the millivolt signal into a digital signal. The digital signal may be read directly by the microprocessor.

Figure 3:
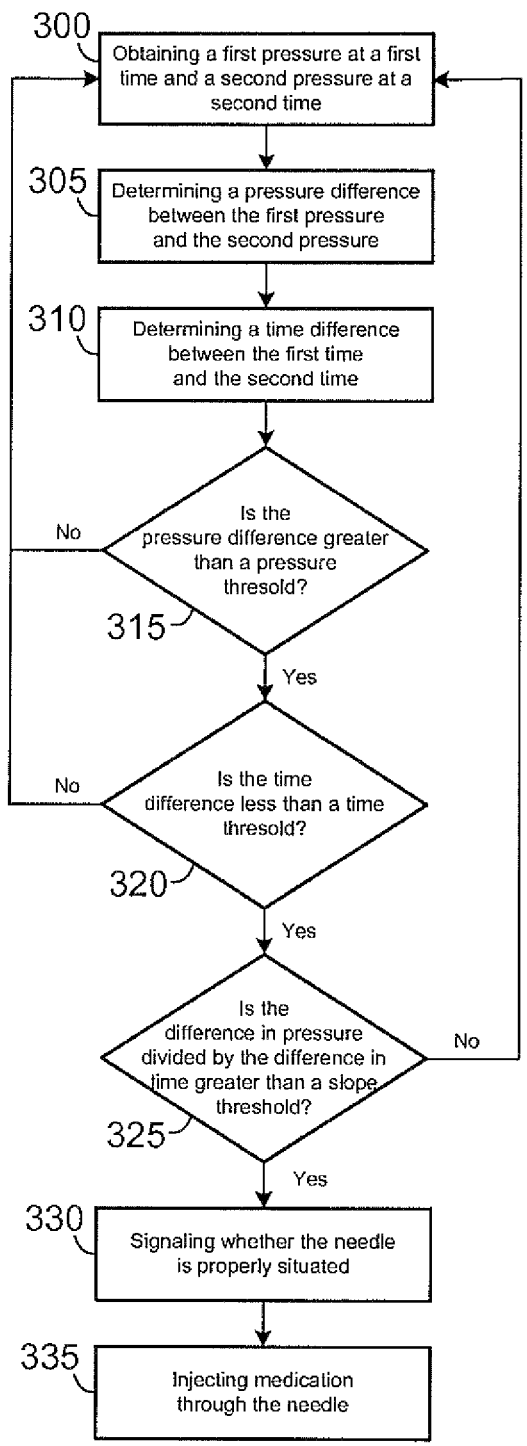
FIG. 3 depicts a method of using a pressure detection device according to an embodiment.

FIG. 3 depicts a method of using a pressure detection device according to an embodiment. A standard injection needle instrumented with the device's pressure transducer and data acquisition system may be used to monitor the pressure as the needle is inserted in the synovial space or joint cavity. The device may be capable of measuring pressure changes in a range of approximately −20 mmHg to approximately 20 mmHg.

In an embodiment, the pressure may be obtained 300 in real-time. For example, the pressure in the joint cavity may be recorded as the needle enters the cavity. Because the actual pressure is transient in nature, the pressure reading may include not just the absolute value of the pressure, but the change in pressure over time. An absolute reading can be insufficient because the pressure may need to change within a certain amount of time. For example, both an initial pressure at an initial time and a resultant pressure at a resultant time may be used to determine a slope of the transient pressure change 300. In an embodiment, the combination of the rate of pressure change as well as the magnitude of the pressure may be used to determine if the device is properly positioned. In an embodiment, proper positioning may also be determined by measuring the pressure at a time after the pressure drop to determine if the pressure remains relatively steady.

A pressure difference may be determined between a first and a second pressure 305. The transient pressure change may be determined by reading the pressure over a period of time. The pressure change, in the joint cavity, may be in a range from approximately −0.2 mmHg to approximately −10 mmHg. In an embodiment, when the needle enters a joint cavity, the pressure may decrease approximately 0.2 mmHg. A first pressure may be measured at or above the baseline pressure. The second pressure may be measured at a negative pressure reading. In an embodiment, the first pressure reading may be at or above atmospheric pressure and the second pressure reading may be approximately 0.2 mmHg below atmospheric pressure. In an embodiment, detection that the needle has entered a joint cavity may include a combination of a rapid drop in pressure with a final pressure magnitude of at least approximately 0.2 mmHg below atmospheric pressure. In an embodiment, the second pressure in the joint cavity may need to be below a certain pressure value. The pressure value may be approximately −0.2 mmHg.

In an embodiment, when the needle enters the epidural space, a negative pressure may occur as compared to the atmospheric pressure. The pressure change, in the epidural space, may be in a range from approximately −0.2 mmHg to approximately −15 mmHg. In an embodiment, the first pressure reading may be at or above atmospheric pressure and the second pressure reading may be approximately 10 mmHg below atmospheric pressure.

A time difference may be determined between a first time and a second time 310. In an embodiment, the time threshold for either the joint cavity or the epidural space may be a range from approximately 0.05 seconds to approximately 0.4 seconds. In an alternate embodiment, the time threshold may be a range from approximately 0.05 seconds to approximately 0.2 seconds.

If the pressure difference is not greater than a pressure threshold 315, than a new pressure may be obtained. In an embodiment, the pressure threshold for the joint cavity may be approximately 0.2 mmHg. In an embodiment, the pressure threshold for the epidural space may be approximately 10 mmHg. If the pressure difference is greater than the pressure threshold 315, than it may be determined whether the time difference is less than a time threshold 320.

In an embodiment, a slope may be determined. The slope may be determined by determining the difference in pressure over the difference in time. In an embodiment, the slope for the joint cavity and/or epidural space may range from approximately −1 to approximately −8. In an embodiment, the slope threshold for a joint cavity and/or epidural space may be less than or equal to approximately −1. In an embodiment, the slope threshold for a joint cavity and/or epidural space may be less than or equal to approximately −1.5.

Based on one or more determinations, the device may signal that the needle is properly situated 330 and medication may be injected 335 through the needle. For example, the device may signal that the needle is properly situated when the pressure difference is greater than a pressure threshold and the time difference is less than a time threshold. In an embodiment, the device may signal that the needle is properly situated when the determined slope is less than a slope threshold. In an embodiment, the device may signal that the needle is properly situated when the second pressure is below a pressure value.

In an embodiment, the pressure may be tested at a third time to determine if the pressure remains at or below a pressure threshold for a time threshold. In an embodiment, the third pressure in a joint cavity may need to remain at or below approximately −0.2 mmHg for at least approximately 0.1 seconds to approximately 0.5 seconds. In an embodiment, the device may signal that the needle is properly situated if the pressure is less than or equal to the pressure threshold and the time is greater than or equal to the time threshold.

An absolute reading can be insufficient because the pressure may return to its original amount within a second or two. However, by looking at the pressure over a period of time, a physician may determine that the needle is in the proper location. For example, if the pressure has a steep slope and the pressure stays elevated or depressed for a certain amount of time, such as, for example, as least approximately 0.1 seconds, then the physician will know that the needle is located in the proper place in the joint cavity.

Figure 4:
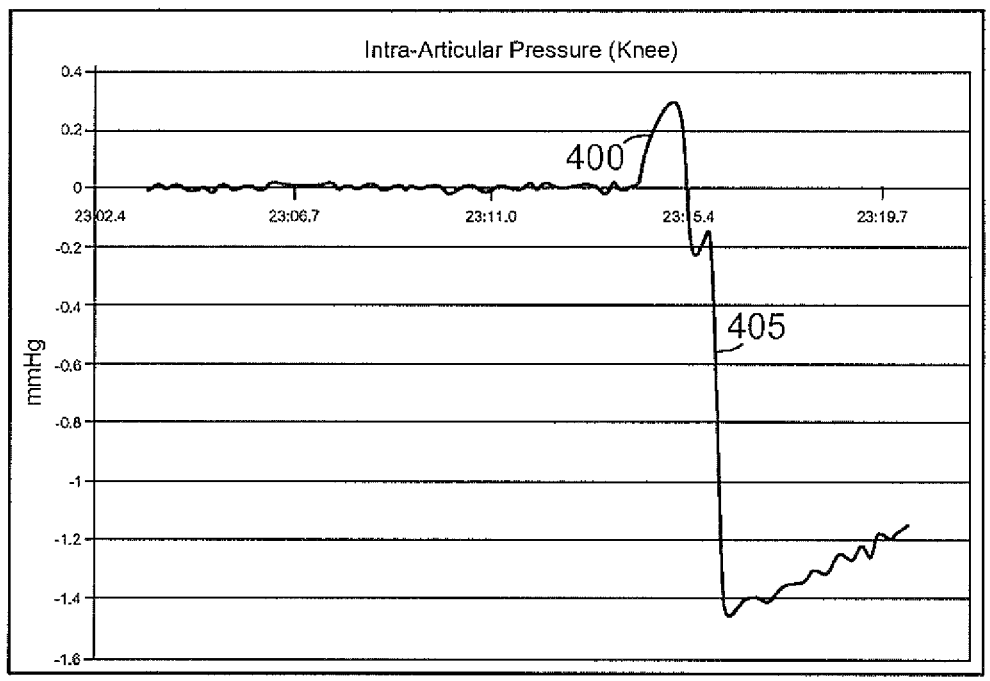
FIG. 4 illustrates an exemplary graph of intra-articular (knee) pressure according to an embodiment.

FIG. 4 illustrates an exemplary graph of intra-articular (knee) pressure according to an embodiment. The graph may depict a slight increase 400 in pressure as the tissue is penetrated and then a sharp decrease 405 in pressure. In an embodiment, a negative pressure may occur when a dry osteoarthritic joint cavity is entered. In FIG. 4, one can determine that the needle has entered the joint cavity because the device detected a steep negative slope of pressure change where the pressure dropped from atmospheric pressure to at least approximately −0.2 mmHg in less than approximately 0.2 seconds. After the pressure dropped, the pressure may remain below approximately −0.2 mmHg for at least approximately 0.2 seconds.

In an embodiment, internal air volume may be taken into account when the pressure is read. In an embodiment, the internal air volume may be less than approximately 0.5 mL. In an embodiment, the internal air volume may be approximately 0.25 mL. The internal air volume may be smaller than the volume of the joint cavity. The internal air volume may be small so that the equalized pressure between the air (at atmospheric pressure) and the negative pressure in the joint cavity equalizes at a pressure similar to the pressure in the joint cavity before the needle tip entered. In an embodiment, the air volume of may be small to ensure that the volume does not affect the measurement of the pressure in the joint cavity upon the needle tip entering.

In an embodiment, a rate of change determination may be calculated to address any compression effects in the air volume of the system. This determination may be used to correct for the error introduced by the dead volume in a syringe and/or needle with the device.

Referring back to FIG. 2, the device may include a power source 210. The power source 210 may be used to power one or more electronic components in the device. In an embodiment, the power source 210 may be used to power all electronic components in the device. In an embodiment, the power source may be a battery 210. The output of the power source 210 may be a nominal voltage based on the type of battery selected. In an embodiment, the actual voltage of a battery may drop based on the amount of current the power source 210 is required to produce. In an embodiment, the battery may need to be electronically isolated from the remaining circuitry until the device is to be used so that the quiescent current draw of the components does not drain the battery prior to usage.

In an embodiment, there may be a self-checking feature for the battery. The self-checking feature may allow a person using the device to determine if the battery is functional and/or monitor the battery voltage. In an embodiment, the self-checking feature may be a signal, such as a light from a light emitting diode or an audible signal.

In an embodiment, the device may include a voltage reference 215. In an embodiment, the pressure transducer 205 may receive a constant voltage. The constant voltage may be provided by a voltage reference 215 which receives battery voltage and regulates it to create a constant output. In an embodiment, changes in applied pressure to the pressure transducer 205 may cause changes in electrical resistance. These changes in electrical resistance cause slight output voltage changes which can be detected and measured. The voltage changes may be directly correlated to the applied pressure.

In an embodiment, the device may include a control microprocessor 220. The control microprocessor 220 may be the decision making component of the device. The control microprocessor 220 may receive the voltage signal from the pressure transducer 205 (or associated intermediate circuitry 230) as an input, and use this information along with decision-making algorithms coded in embedded firmware to determine whether the needle is properly positioned. In an embodiment, the microprocessor 220 may measure the change in voltage from the pressure transducer 205 via an analog to digital conversion. In an embodiment, the microprocessor 220 may store the transient pressure readings. In an embodiment, the stored pressure readings may be retrieved by any means known in the art such as, but not limited to, a wireless or a connected interface. In an embodiment, a properly positioned needle may be located within the synovial space. Once the microprocessor 220 determines that the needle is properly positioned, the microprocessor may output a signal to the user interface 225.

In an embodiment, the device may include a user interface 225. The user interface 225 may be used to inform a physician when the needle is properly placed in a patient. In an embodiment, a user interface 225 may include a light emitting diode (LED). The user interface 225 may receive a signal from the microprocessor in order to power the LED. In an embodiment, the LED may be used to indicate states of the device, such as, but not limited to, power up or error. In an embodiment, the brightness of the LED may be observed from a distance of approximately 4 ft. A user interface 225 may be in a location so that it can easily be viewed by a physician while holding the syringe to perform an injection. As a user interface 225 is used to inform a physician that the needle is properly positioned, the device may be used ambidextrously.

In an embodiment, the user of the device may be a trained physician who delivers the medication. A medical staff person may be trained to prepare for the injection by attaching the device between the syringe and the injection needle. In an embodiment, the LED on the device may be used during set-up to alert the staff person that the device is on and properly functioning.

In an embodiment, the user interface 225 may alert a user by illuminating one or more LEDs. In an embodiment, the one or more LEDs may be multicolored. A multicolored LED may be used to differentiate various states to the user. For example, one color may indicate that the device is on, while another color may indicate that the needle is properly positioned within the patient's joint.

In an embodiment, the user interface 225 may include an audible signal. The audible signal may indicate that the device is working, that the device has a malfunction and/or that the device is in the proper location inside a patient. In an embodiment, an audible signal may be used in conjunction with one or more LEDs.

In an embodiment, the device may include intermediate circuitry 230. Intermediate circuitry 230 may be included between the components already described. Intermediate circuitry 230 may include, but is not limited to, an amplifier, a filter and/or signal processing circuitry. An amplifier may be used to raise the transducer output voltage to a level to be more easily measured by the microprocessor. A filter may be used to reduce any system noise which may compromise the pressure transducer signal. Signal processing circuitry may be used to ensure that the signal is compatible with the microprocessor.

In an embodiment, the device may include a microsensor. In an embodiment, the microsensor may be a solid state or microelectromechanical system capable of producing an electrical signal relative to the range of desired pressures.

In an embodiment, the device may used in a clinical environment, such as, but not limited to, hospitals, physician offices or healthcare clinics. The primary users of the device may be physicians, surgeons, nurse practitioners and/or other trained medical personnel.

In an embodiment, the device may be used to inject the medication. If the device is independent, the entire unit may be disposed. If the device is embedded in the syringe, for procedures such as, but not limited to, epidural anesthesia, the syringe may be removed in order to precisely deliver the anesthetic agent to the proper location.

In an embodiment, the device may be transported from a manufacturing or storage facility to a hospital or clinic by shipping via standard freight carriers. In an embodiment, the device housing may comply with mechanical strength requirements, such as, but not limited to, impact and rough handling.

In an embodiment, the device may be designed to be operated in an operating room environment. In an embodiment, the device may be operated within the temperature range of approximately 0° C. to approximately 40° C. The device may be stored and shipped within the temperature range of approximately −40° C. to approximately 70° C.

In an embodiment, the device may have a useful operational life of a minimum of 1 minute after being energized by the user. In an embodiment, the device may have a shelf life of at least 6 months. In an embodiment, the device may be packaged in sterile, individual packages. In an embodiment, the device may be sterilized by exposure to gamma radiation and/or ethylene oxide.

In an embodiment, the device shall be designed such that the user can determine if hardware failures have occurred (e.g., failure to energize due to a dead battery).

In an embodiment, a system may include a pressure detection device and a computing system. The pressure detection device may have a first locking mechanism configured to connect a first end of the device to a needle and a second locking mechanism configured to connect a second end of the device to a syringe. The device may also include a pressure transducer configured to measure a first pressure at a first time and a second pressure at a second time. The pressure transducer may transmit the pressure and the times to a computing system.

Figure 5:
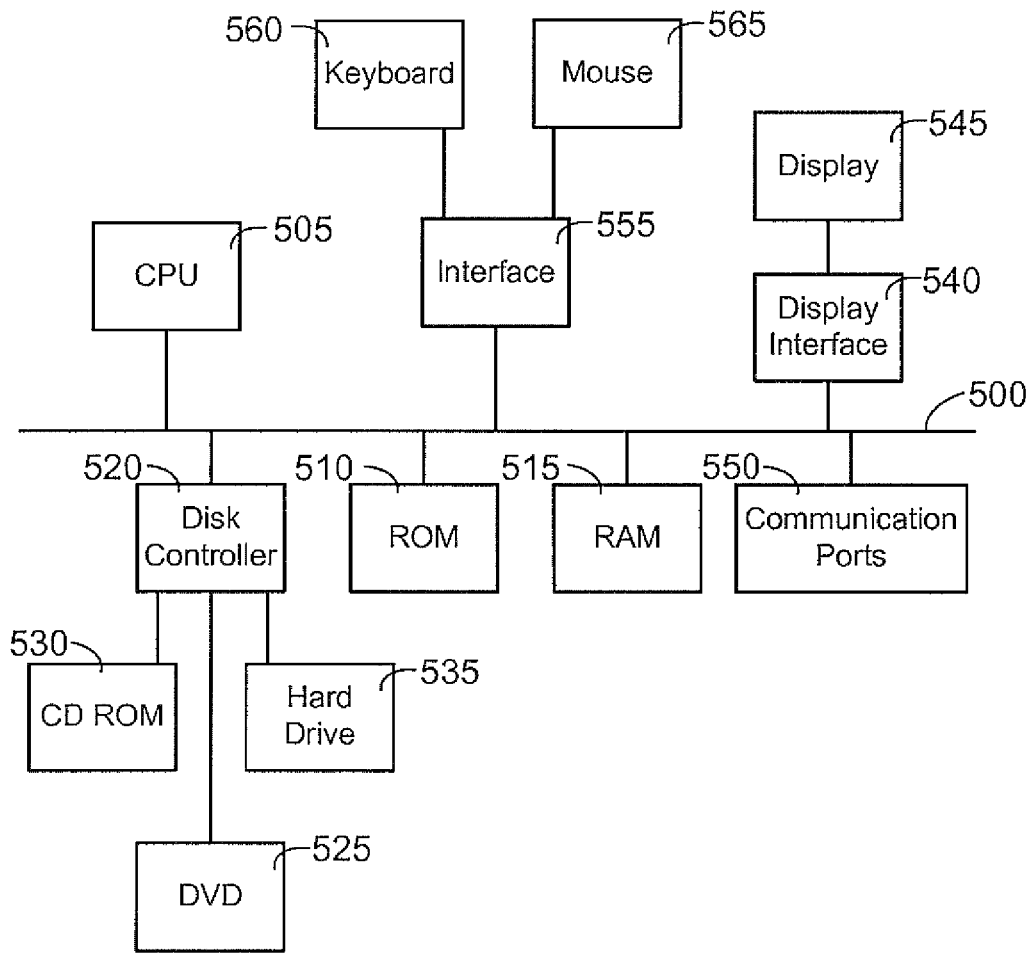
FIG. 5 depicts a block diagram of an exemplary computing system that may be used to contain or implement program instructions according to an embodiment.

FIG. 5 depicts a block diagram of an exemplary computing system that may be used to contain or implement program instructions according to an embodiment. Referring to FIG. 5, a bus 500 serves as the main information highway interconnecting the other illustrated components of the hardware. CPU 505 is the central processing unit of the system, performing calculations and logic operations required to execute a program. Read only memory (ROM) 510 and random access memory (RAM) 515 constitute exemplary memory devices or storage media.

A disk controller 520 interfaces with one or more optional disk drives to the system bus 500. These disk drives may include, for example, external or internal DVD drives 525, CD ROM drives 530 or hard drives 535. As indicated previously, these various disk drives and disk controllers are optional devices.

Program instructions may be stored in the ROM 510 and/or the RAM 515. Optionally, program instructions may be stored on a computer readable storage medium, such as a hard drive, a compact disk, a digital disk, a memory or any other tangible recording medium.

An optional display interface 540 may permit information from the bus 500 to be displayed on the display 545 in audio, graphic or alphanumeric format. Communication with external devices may occur using various communication ports 550.

In addition to the standard computer-type components, the hardware may also include an interface 555 which allows for receipt of data from input devices such as a keyboard 560 or other input device 565 such as a mouse, remote control, touch pad or screen, pointer and/or joystick.

In an embodiment, the computing system may signal when the needle is properly situated based on the pressure and time determinations. In an embodiment, the computing system may be configured to light an LED or produce an audible sound from the computing device when the needle is properly situated. In an embodiment, the computing device may transmit a signal to the pressure detection device to cause the pressure detection device to light an LED or produce an audible sound when the needle is properly situated.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which are also intended to be encompassed by the following claims.

The invention claimed is:

1. A method of using a pressure detection device comprising:
obtaining, by a processing device, a first pressure at a first time and a second pressure at a second time in real time via a pressure transducer, wherein the first pressure and the second pressure each, individually, represent a pressure of an area at a tip of a needle, and wherein the first time and the second time occur while inserting the needle into a joint cavity;
determining, by the processing device, a pressure difference between the first pressure and the second pressure, wherein the pressure difference represents a difference between a pressure in a cavity and atmospheric pressure;

determining, by the processing device, a time difference between the first time and the second time;

performing, by the processing device, a first determination to determine whether the pressure difference divided by the time difference is less than a slope threshold; and providing an indication to inject a medication.

2. The method of claim 1 wherein the pressure detection device is positioned between a syringe and an injection needle hub.

3. The method of claim 1 wherein providing an indication comprises one or more of the following:

displaying a light from a light emitting diode; and producing an audible sound.

4. The method of claim 1, further comprising:

storing, by the processing device, the first pressure; and retrieving, by the processing device, the stored first pressure to display on a user interface.

5. The method of claim 1, further comprising:

performing, by the processing device, a pressure threshold determination to determine whether the pressure difference exceeds a pressure threshold; and performing, by the processing device, a time threshold determination to determine whether the time difference is less than a time threshold, wherein providing an indication is further based on the pressure threshold determination and the time threshold determination.

6. The method of claim 5, further comprising:

determining, by the processing device, whether the second pressure is less than a pressure value, wherein providing an indication is further based on whether the second pressure is less than the pressure value.

7. The method of claim 1, further comprising:

determining, by the processing device, an internal air volume inside the pressure detection device, wherein the internal air volume is less than 0.5 mL.

8. The method of claim 1 wherein the slope threshold is approximately −1.5.

9. The method of claim 1, further comprising:

obtaining, by the processing device, a third pressure at a third time wherein the third pressure represents the pressure of an area at the tip of the needle;

performing, by the processing device, a second determination to determine whether the third pressure is less than a pressure threshold; and performing, by the processing device, a third determination to determine whether a second time difference between the second time and the third time is greater than a time threshold, wherein providing an indication is further based on the second determination and the third determination.

10. The method of claim 9 wherein the time threshold is approximately 0.1 seconds.

11. The method of claim 9 wherein the pressure threshold is approximately −0.2 mmHg.

12. The method of claim 1, wherein providing the indication comprises providing the indication to inject the medication when the first determination indicates that the needle is properly situated in the cavity based on the pressure difference being greater than a pressure threshold and the time difference being less than a time threshold.

13. A method of using a pressure detection device comprising:

obtaining, by a processing device, a first pressure at a first time and a second pressure at a second time in real time via a pressure transducer, wherein the first pressure and the second pressure each, individually, represent a pressure of an area at a tip of a needle, and wherein the first time and the second time occur while inserting the needle into an epidural cavity;

determining, by the processing device, a pressure difference between the first pressure and the second pressure, wherein the pressure difference represents a difference between a pressure in a cavity and atmospheric pressure;

determining, by the processing device, a time difference between the first time and the second time;

performing, by the processing device, a first determination to determine whether the pressure difference divided by the time difference is less than a slope threshold; and providing an indication to inject a medication.

14. The method of claim 13 wherein the pressure detection device is positioned between a syringe and an injection needle hub.

15. The method of claim 13 wherein providing an indication comprises one or more of the following:

displaying a light from a light emitting diode; and producing an audible sound.

16. The method of claim 13, further comprising:

storing, by the processing device, the first pressure; and retrieving, by the processing device, the stored first pressure to display on a user interface.

17. The method of claim 13, further comprising:

performing, by the processing device, a pressure threshold determination to determine whether the pressure difference exceeds a pressure threshold; and performing, by the processing device, a time threshold determination to determine whether the time difference is less than a time threshold, wherein providing an indication is further based on the pressure threshold determination and the time threshold determination.

18. The method of claim 17, further comprising:

determining, by the processing device, whether the second pressure is less than a pressure value, wherein providing an indication is further based on whether the second pressure is less than the pressure value.

19. The method of claim 13, further comprising:

determining, by the processing device, an internal air volume inside the pressure detection device, wherein the internal air volume is less than 0.5 mL.

20. The method of claim 13, further comprising:

obtaining, by the processing device, a third pressure at a third time wherein the third pressure represents the pressure of an area at the tip of the needle;

performing, by the processing device, a second determination to determine whether the third pressure is less than a pressure threshold; and performing, by the processing device, a third determination to determine whether a second time difference between the second time and the third time is greater than a time threshold, wherein providing an indication is further based on the second determination and the third determination.

21. The method of claim 13, wherein providing the indication comprises providing the indication to inject the medication when the first determination indicates that the needle is properly situated in the cavity based on the pressure difference being greater than a pressure threshold and the time difference being less than a time threshold.

* * * * *